United States Patent
Kim et al.

(10) Patent No.: US 9,254,113 B2
(45) Date of Patent: Feb. 9, 2016

(54) X-RAY IMAGING APPARATUS AND METHOD OF CONTROLLING THE SAME

(71) Applicant: SAMSUNG ELECTRONICS CO., LTD., Suwon-si (KR)

(72) Inventors: Sung Su Kim, Yongin-si (KR); Hyun Hwa Oh, Hwaseong-si (KR); Dong Goo Kang, Suwon-si (KR); Sung Hoon Kang, Suwon-si (KR); Young Hun Sung, Hwaseong-si (KR); Kang Eui Lee, Seoul (KR); Seok Min Han, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 88 days.

(21) Appl. No.: 14/100,123

(22) Filed: Dec. 9, 2013

(65) Prior Publication Data

US 2014/0185760 A1 Jul. 3, 2014

(30) Foreign Application Priority Data

Dec. 28, 2012 (KR) .................. 10-2012-0156718

(51) Int. Cl.
  *A61B 6/00* (2006.01)
  *A61B 6/04* (2006.01)

(52) U.S. Cl.
  CPC ............ *A61B 6/5294* (2013.01); *A61B 6/0414* (2013.01); *A61B 6/4241* (2013.01); *A61B 6/482* (2013.01); *A61B 6/502* (2013.01); *A61B 6/5258* (2013.01); *A61B 6/583* (2013.01)

(58) Field of Classification Search
  CPC .... A61B 6/0414; A61B 6/4241; A61B 6/482; A61B 6/502; A61B 6/5258; A61B 6/5294; A61B 6/583; G06F 17/5036; H01J 37/32091; H01J 37/32422
  USPC ........................................ 378/19, 37, 62, 98.8
  See application file for complete search history.

(56) References Cited

U.S. PATENT DOCUMENTS

| | | | |
|---|---|---|---|
| 5,774,522 A | 6/1998 | Warburton | |
| 7,850,367 B2 | 12/2010 | Takenaka et al. | |
| 8,605,857 B1 * | 12/2013 | Renner | 378/65 |
| 2002/0025018 A1 * | 2/2002 | Takagi et al. | 378/8 |
| 2003/0016778 A1 * | 1/2003 | Tachizaki et al. | 378/4 |
| 2004/0081281 A1 * | 4/2004 | Fadler et al. | 378/98.12 |
| 2008/0075227 A1 * | 3/2008 | Christoph et al. | 378/23 |

FOREIGN PATENT DOCUMENTS

| | | | |
|---|---|---|---|
| KR | 1020060051425 A | 5/2006 | |
| KR | 101092216 B1 | 12/2011 | |

* cited by examiner

*Primary Examiner* — Irakli Kiknadze
(74) *Attorney, Agent, or Firm* — Sughrue Mion, PLLC

(57) ABSTRACT

The X-ray imaging apparatus includes an X-ray generator to generate and emit X-rays, an X-ray detector to detect the emitted X-rays and acquire X-ray data, and a controller to convert the X-ray data into X-ray characteristic coordinates and estimate a response characteristic function of the X-ray detector from a relationship between measurement data and reference data, the measurement data and the reference data being converted into the X-ray characteristic coordinates.

19 Claims, 17 Drawing Sheets

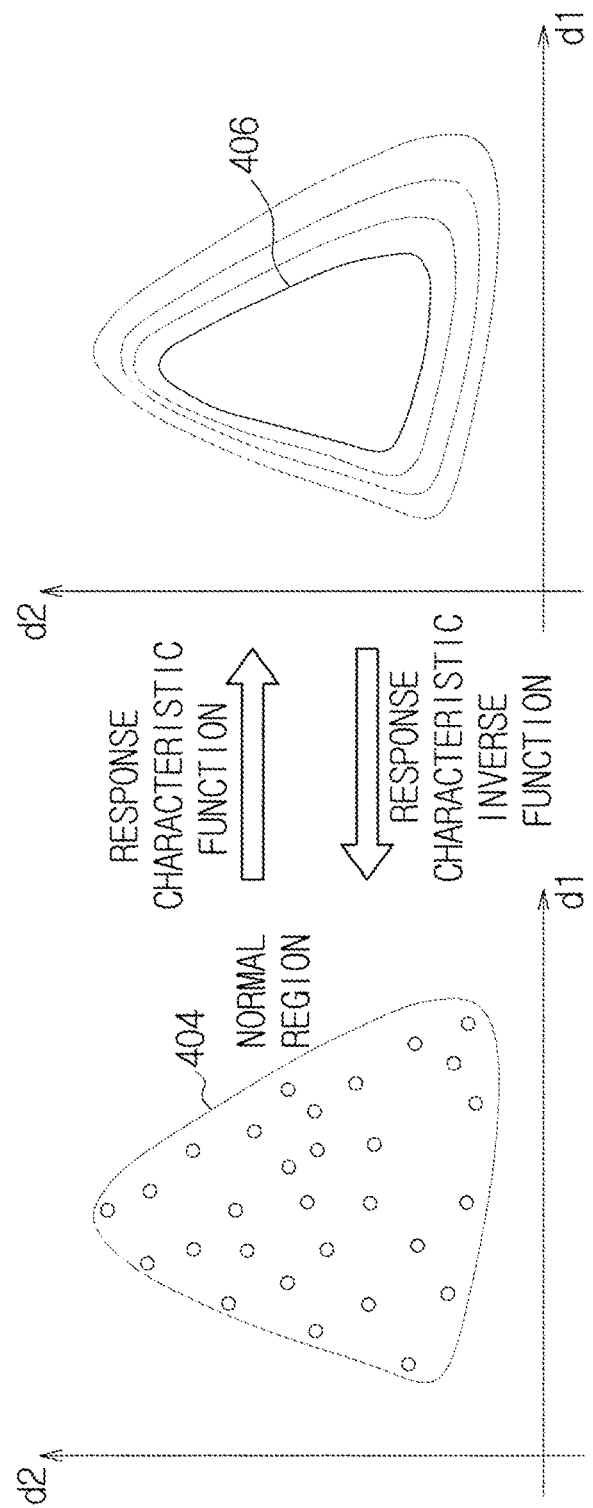

X-RAY IMAGING APPARATUS AND METHOD OF CONTROLLING THE SAME

CROSS-REFERENCE TO RELATED APPLICATION

This application claims priority from Korean Patent Application No. 10-2012-0156718, filed on Dec. 28, 2012 in the Korean Intellectual Property Office, the disclosure of which is incorporated herein by reference in its entirety.

BACKGROUND

1. Field

Apparatuses and methods consistent with exemplary embodiments relate to an X-ray imaging apparatus and a method of controlling the same, and more particularly, to an X-ray imaging apparatus which passes multiple-energy band X-rays through an object to generate an X-ray image and a method of controlling the same.

2. Description of the Related Art

An X-ray imaging apparatus irradiates an object with X-rays and analyzes X-rays having passed through the object to examine an internal structure of the object. X-ray permeability may differ according to tissues constituting the object. Thus, intensity of X-rays having passed through the object is detected to image the internal structure of the object.

In detail, an X-ray generator generates X-rays and irradiates the object with the X-rays. Then, an X-ray detector detects X-rays having passed through the object, converts the detected X-rays into an electrical signal, and transmits the electrical signal to a controller.

The controller generates an X-ray image of the object using the electrical signal transmitted from the X-ray detector. Image quality, resolution, accuracy, or the like of the X-ray image may differ according to the response characteristics of the X-ray detector.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide an X-ray imaging apparatus and a method of controlling the same, which estimate the energy response characteristics of an X-ray detector and correct distortion of X-ray data based on the estimated response characteristic.

In accordance with an aspect of an exemplary embodiment, an X-ray imaging apparatus includes an X-ray generator to generate and emit X-rays, an X-ray detector to detect the emitted X-rays and acquire X-ray data, and a controller to convert measurement data acquired by detecting X-rays by the X-ray detector and reference data acquired via simulation into X-ray characteristic coordinates as coordinates on a predefined space and to estimate a response characteristic function of the X-ray detector from a relationship between the reference data and X-ray data, the measurement data and the reference dare being converted into the X-ray characteristic coordinates.

In accordance with an aspect of an exemplary embodiment, a method of controlling an X-ray imaging apparatus includes acquiring measurement data and reference data under the same response characteristic parameter condition, converting each of the measurement data and the reference data into X-ray characteristic coordinates as coordinates on a predefined space, and estimating a response characteristic function of an X-ray detector from a relationship between the measurement data and the reference data, the measurement data and reference data being converted into the X-ray characteristic coordinates.

The acquiring of the measurement data and the reference data may include setting the response characteristic parameter to a specific value and irradiating an X-ray phantom with X-rays, and detecting X-rays having passed through the X-ray phantom to acquire X-ray data.

BRIEF DESCRIPTION OF THE DRAWINGS

The above and/or other aspects will become more apparent by describing certain exemplary embodiments, with reference to the accompanying drawings in which:

FIG. 9 is a schematic diagram showing a relationship between a function estimated by a response characteristic estimator and a function used by a coordinate corrector;

DETAILED DESCRIPTION

Figure 1:
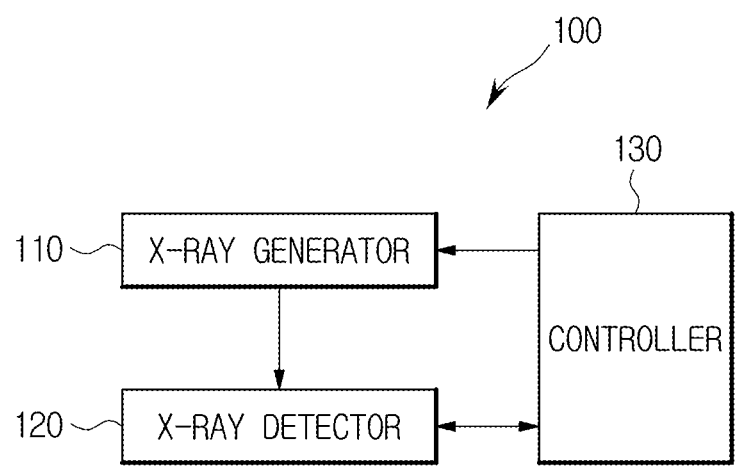
FIG. 1 is a control block diagram of an X-ray imaging apparatus.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Figure 2:
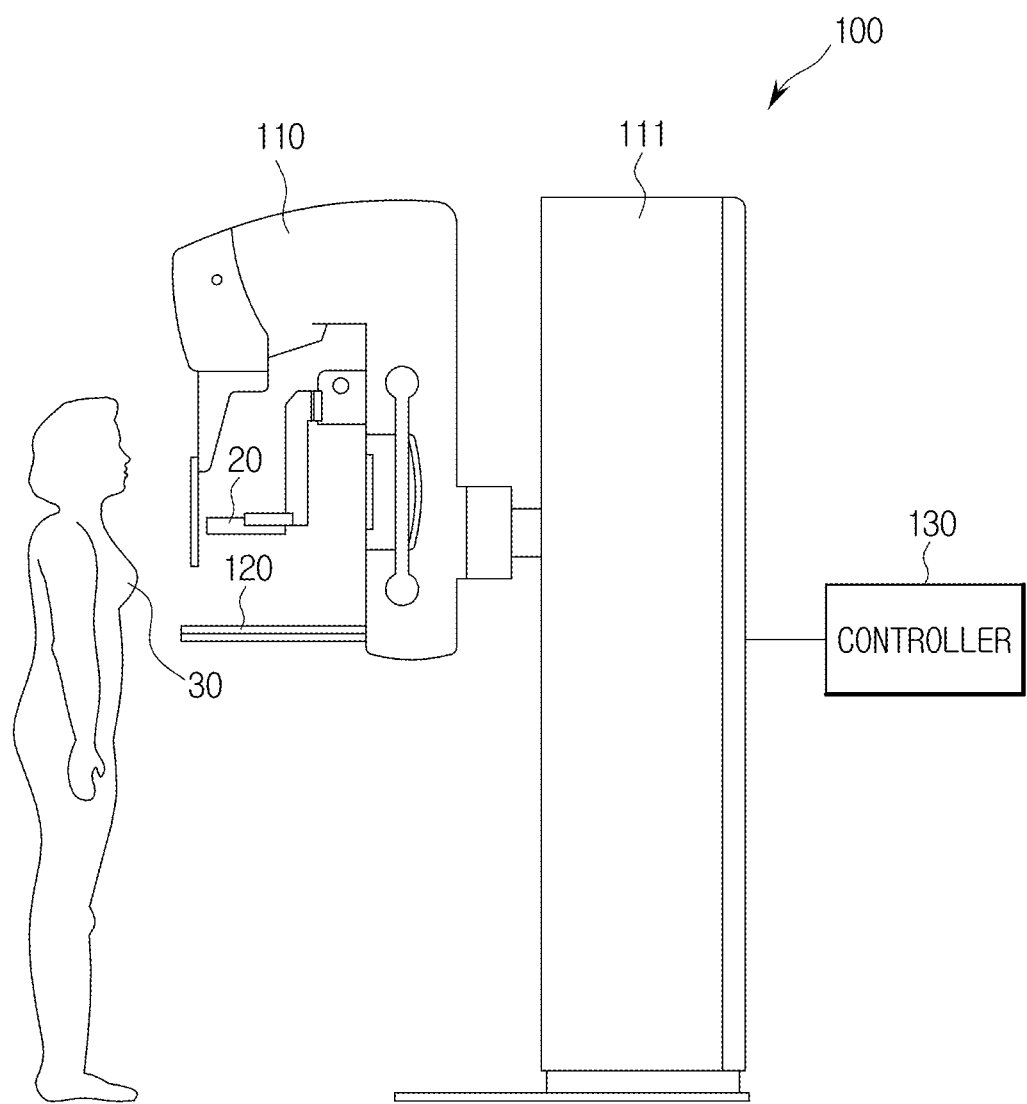
FIG. 2 is a diagram of an overall outer appearance of an X-ray imaging apparatus for mammography.

FIG. 1 is a control block diagram of an X-ray imaging apparatus 100 and FIG. 2 is a diagram of an overall appearance of an X-ray imaging apparatus for mammography.

A structure, a control condition, or the like of the X-ray imaging apparatus 100 slightly differs according to an object to be imaged. According to exemplary embodiments, the object to be imaged by the X-ray imaging apparatus 100 is not particularly limited. However, for detailed description, FIG. 2 illustrates the X-ray imaging apparatus 100 for mammography.

Referring to FIGS. 1 and 2, the X-ray imaging apparatus 100 includes an X-ray generator 110 to generate X-rays and to irradiate an object with the X-rays, an X-ray detector 120 to detect X-rays having passed through the object, and a controller 130 to estimate the response characteristics of the X-ray detector 120 to correct distortion of X-ray data of the X-ray detector 120.

The X-ray generator 110 generates the X-rays and irradiates the object with the X-rays. When the object corresponds to a breast or the breasts 30, the object is positioned between a compression paddle 20 and the X-ray detector 120 and is compressed by the compression paddle 20. In this state, the object is irradiated with the X-rays. The X-ray generator 110 receives power from a power supply (not shown) to generate the X-rays. Energy of the X-rays may be controlled according to an applied tube voltage, and the intensity or dose of the X-rays may be controlled according to tube current and the exposure time of the X-rays.

The X-ray generator 110 and the X-ray detector 120 are mechanically connected to a housing 111. The housing 111 may support the X-ray generator 110 and the X-ray detector 120, and may include a generator.

The X-ray generator 110 may emit monochromatic X-rays or polychromatic X-rays. In the X-ray imaging apparatus 100 according to the present exemplary embodiment, the X-ray generator 110 emits polychromatic X-rays having a specific energy bandwidth and the energy bandwidth of the X-rays is defined by an upper limit and a lower limit.

The upper limit of the energy band, that is, maximum energy of the emitted X-rays may be adjusted according to the amplitude of the tube voltage. The lower limit of the energy band, that is, minimum energy of the emitted X-rays may be adjusted according to a filter installed inside or outside the X-ray generator 110. When X-rays having a low energy bandwidth are filtered by the filter, average X-ray energy may be increased.

The X-ray detector 120 detects the X-rays having passed through the object and converts the detected X-rays into X-ray data.

In general, the X-ray detector 120 may be classified according to a material composition method, a method of converting detected X-rays into an electrical signal, and a method of acquiring the electrical signal. In this regard, hereinafter, various methods of detecting X-rays and converting the X-rays into an electrical signal by the X-ray detector 120 will be described.

For example, the X-ray detector 120 may be a detector including a monolithic type device or a detector including a hybrid type device, according to the material composition method.

When the X-ray detector 120 includes the monolithic type device, a portion to detect X-rays to generate an electrical signal and a portion to read and process the electrical signal are formed of semiconductors formed of the same material or manufactured using the same process, which corresponds to, for example, a case in which a light receiving device such as a charge coupled device (CCD) or a complementary metal oxide semiconductor (CMOS) are used.

When the X-ray detector 120 includes the hybrid type device, a portion to detect X-rays to generate an electrical signal and a portion to read and process the electrical signal are formed of respective different materials or manufactured using different processes, which corresponds to, for example, a case in which a light receiving device such as a photodiode, a CCD, CdZnTe, or the like detects X-rays and a CMOS read out integrated circuit (ROIC) reads and processes an electrical signal, a case in which a strip detector detects X-rays and a CMOS ROIC reads and processes an electrical signal, and a case in which an a-Si or a-Se flat panel system is used.

In addition, the X-ray detector 120 may be a direct conversion type or an indirect conversion type, according to a method of converting X-rays into an electrical signal.

In the direct conversion type, when X-rays are emitted, electron-hole pairs are temporally generated, and electrons are moved to a positive electrode and holes are moved towards a negative electrode according to an electric field applied between opposite ends of a light receiving device. The X-ray detector 120 converts this movement into an electrical signal. In the direct conversion type, the light receiving device is formed of a-Se, CdZnTe, $HgI_2$, $PbI_2$, or the like.

In the indirect conversion type, a scintillator is disposed between a light receiving device and the X-ray generator 110. Thus, when X-rays emitted from the X-ray generator 110 react with the scintillator to emit photons having a visible light wavelength, the light receiving device detects the photons and converts the photons into an electrical signal. In the indirect conversion type, the light receiving device is formed of a-Si or the like, and a thin film type GADOX scintillator, a micro column type scintillator, a needle structure type CSI (T1) scintillator, or the like may be used as the scintillator.

In addition, the X-ray detector 120 may be a charge integration mode type, which stores electric charges for a predetermined period of time to acquire signals from the stored electrical charges, or a photon counting mode type, which counts signals whenever the signals are generated by a single X-ray photon, according to a method of acquiring an electrical signal.

The X-ray imaging apparatus 100 according to an exemplary embodiment may use any of the aforementioned detectors. However, for convenience of description, a case in which the X-ray imaging apparatus 100 uses a direct conversion type in which an electric signal is directly acquired from X-rays, a hybrid method in which a sensor chip to detect X-rays and a read-out circuit chip are integrated with each other, and a photon counting mode will be described in detail with regard to an exemplary embodiment.

Figure 3A:
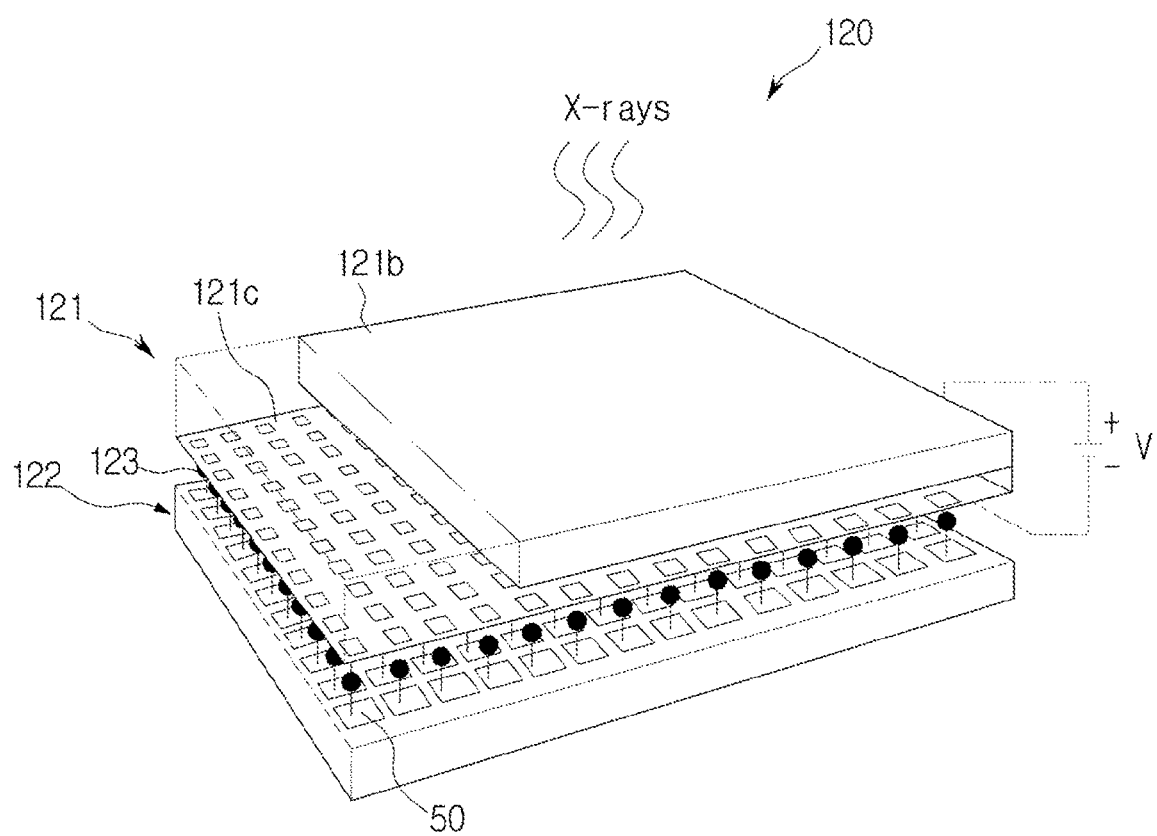
FIG. 3A is a schematic diagram of a structure of an X-ray detector of an X-ray imaging apparatus according to an exemplary embodiment.
Figure 3B:
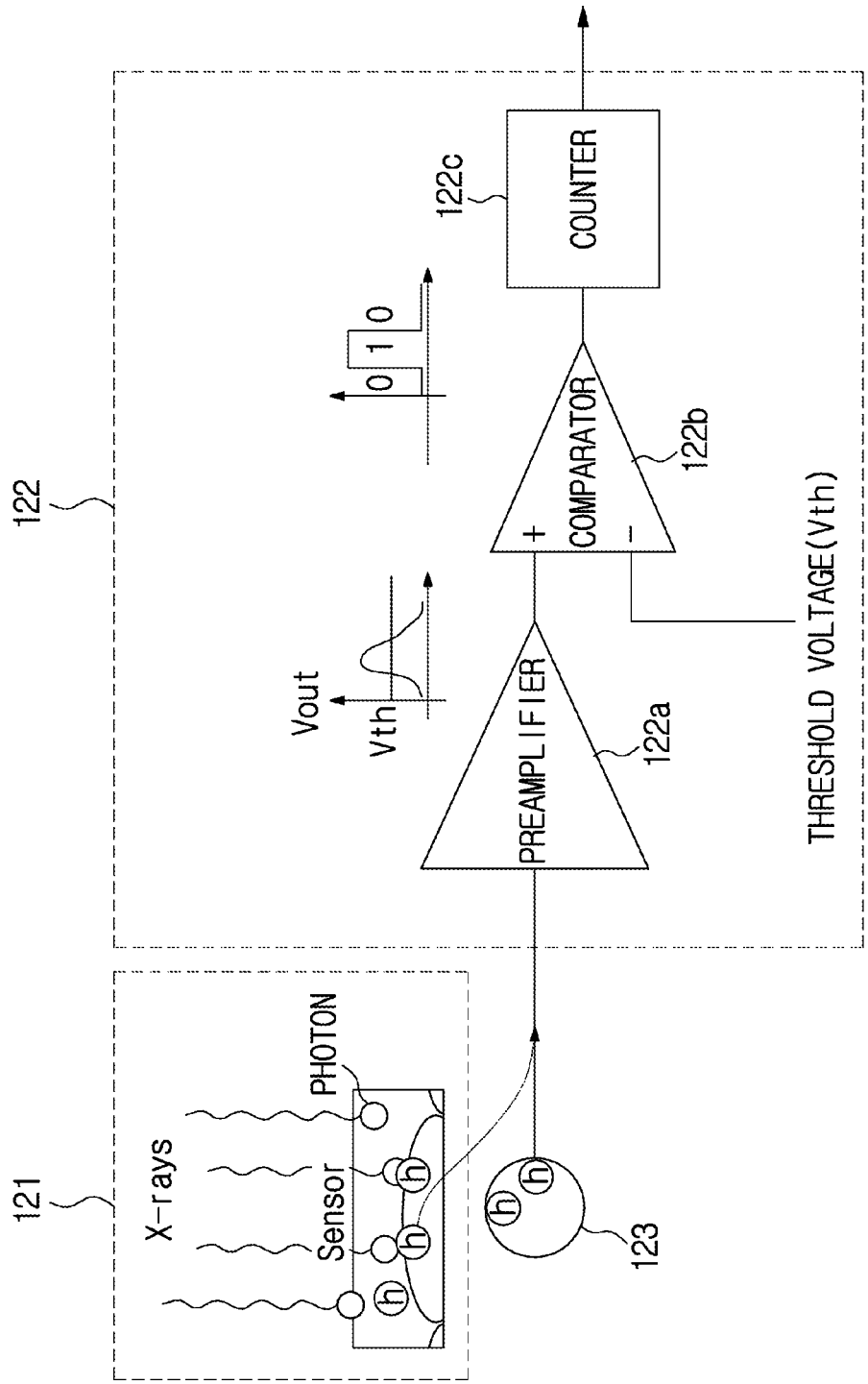
FIG. 3B is a schematic circuit diagram of a single pixel region of an X-ray detector of an X-ray imaging apparatus according to an exemplary embodiment.

FIG. 3A is a schematic diagram of a structure of the X-ray detector 120 of the X-ray imaging apparatus 100 according to an exemplary embodiment and FIG. 3B is a schematic circuit diagram corresponding to a single pixel region of the X-ray detector 120 of the X-ray imaging apparatus 100 according to an exemplary embodiment.

Referring to FIG. 3A, the X-ray detector 120 includes a detection device 121 to detect X-rays to generate an electrical signal and a read-out circuit 122 to read out the generated electrical signal. The detection device 121 is included in a light receiving device. The read-out circuit 122 may be formed as a two-dimensional (2D) pixel array including a plurality of pixel regions 50.

The detection device 121 may be formed of a single crystal semiconductor material in order to ensure high resolution, high response time, and high dynamic range at low energy and low dose. The single crystal semiconductor material may be Ge, CdTe, CdZnTe, GaAs, or the like.

The detection device 121 may be formed as a PIN photodiode by bonding a p-type layer 121c in which p-type semiconductors are arranged in a 2D pixel array to a lower surface of a high resistance n-type semiconductor substrate 121b. The read-out circuit 122 using a CMOS process is coupled to the detection device 121 for each respective pixel or pixel region 50. The CMOS read-out circuit 122 and the detection device 121 may be bonded to each other via a flip chip bonding method. That is, the read-out circuit 122 and the detection device 121 may be bonded to each other by reflowing bumps 123 formed of PbSn, In, or the like therebetween and compressing the read-out circuit 122 and the detection device 121 to each other while applying heat.

When photons of X-rays are incident upon the detection device 121, electrons in a valence band absorb energy of the photons which is equal to or greater than a band-gap energy difference and are excited to a conduction band. Accordingly, electron-hole pairs are generated in a depletion region.

A metal electrode is formed at each of the p-type layer 121c and the n-type semiconductor substrate 121b of the detection device 121. When a reverse bias is applied between metal electrodes, electrons of the electron-hole pairs generated in the depletion region are attracted toward an n-type region and holes are attracted toward a p-type region. The holes attracted toward a p-type region are input to the read-out circuit 122 via the bumps 123 so that an electrical signal generated by photons may be read. For example, electrons may be input to the read-out circuit 122 according to the structure of the detection device 121 and an applied voltage so that an electrical signal may be generated.

The read-out circuit 122 may be a 2D pixel array corresponding to the p-type semiconductors of the detection device 121 and may read out an electrical signal for each respective pixel or pixel region 50. Referring to FIG. 3B, when electric charges are input to the read-out circuit 122 from the detection device 121 via the bumps 123, a preamplifier 122a of the read-out circuit 122 is charged with an input electric charge generated from a single photon and outputs a voltage signal corresponding thereto.

The voltage signal output from the preamplifier 122a is transmitted to a comparator 122b, the comparator 122b compares an externally controllable threshold voltage with the input voltage signal to output a pulse signal of '1' or '0' according to comparison results, and a counter counts the output number of '1' and outputs digitized X-ray data. Thus, the X-ray data output from the X-ray detector 120 includes information regarding the number of photons per pixel.

Figure 4A:
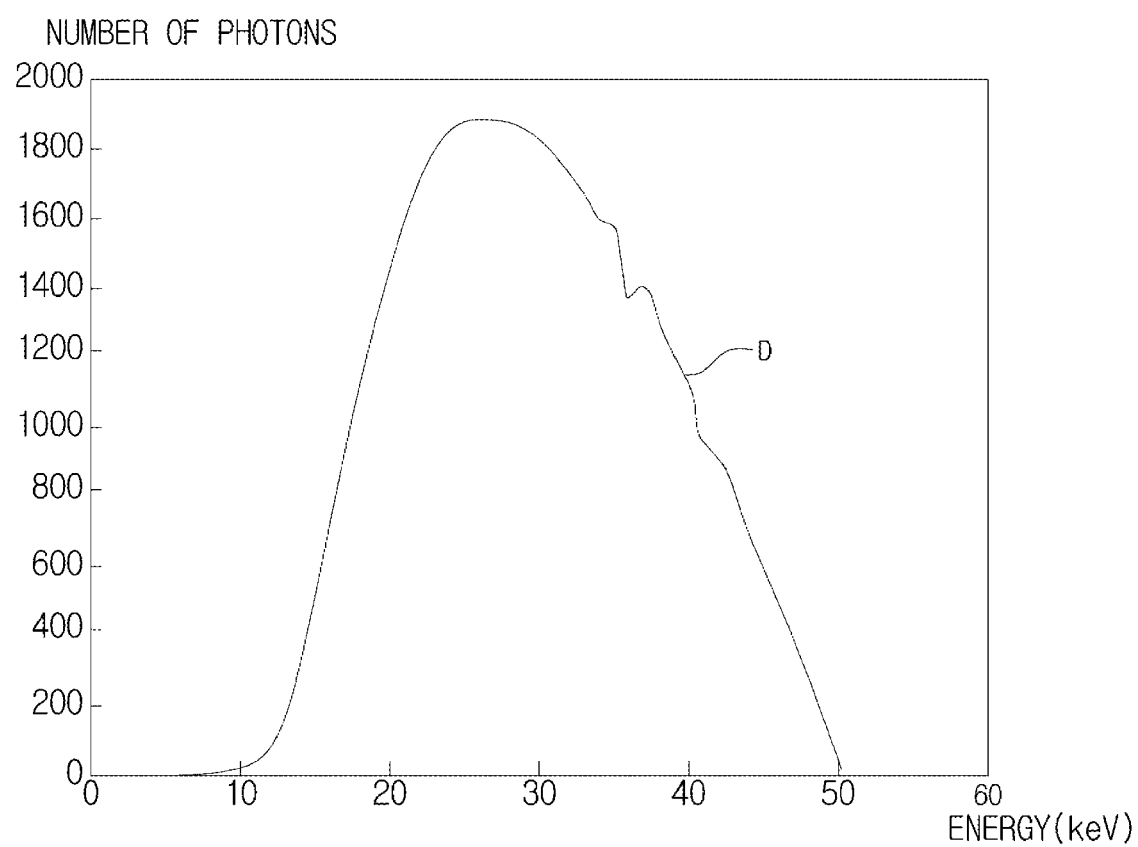
FIG. 4A is a graph showing an energy spectrum of X-rays irradiated by an X-ray generator, according to an exemplary embodiment.
Figure 4B:
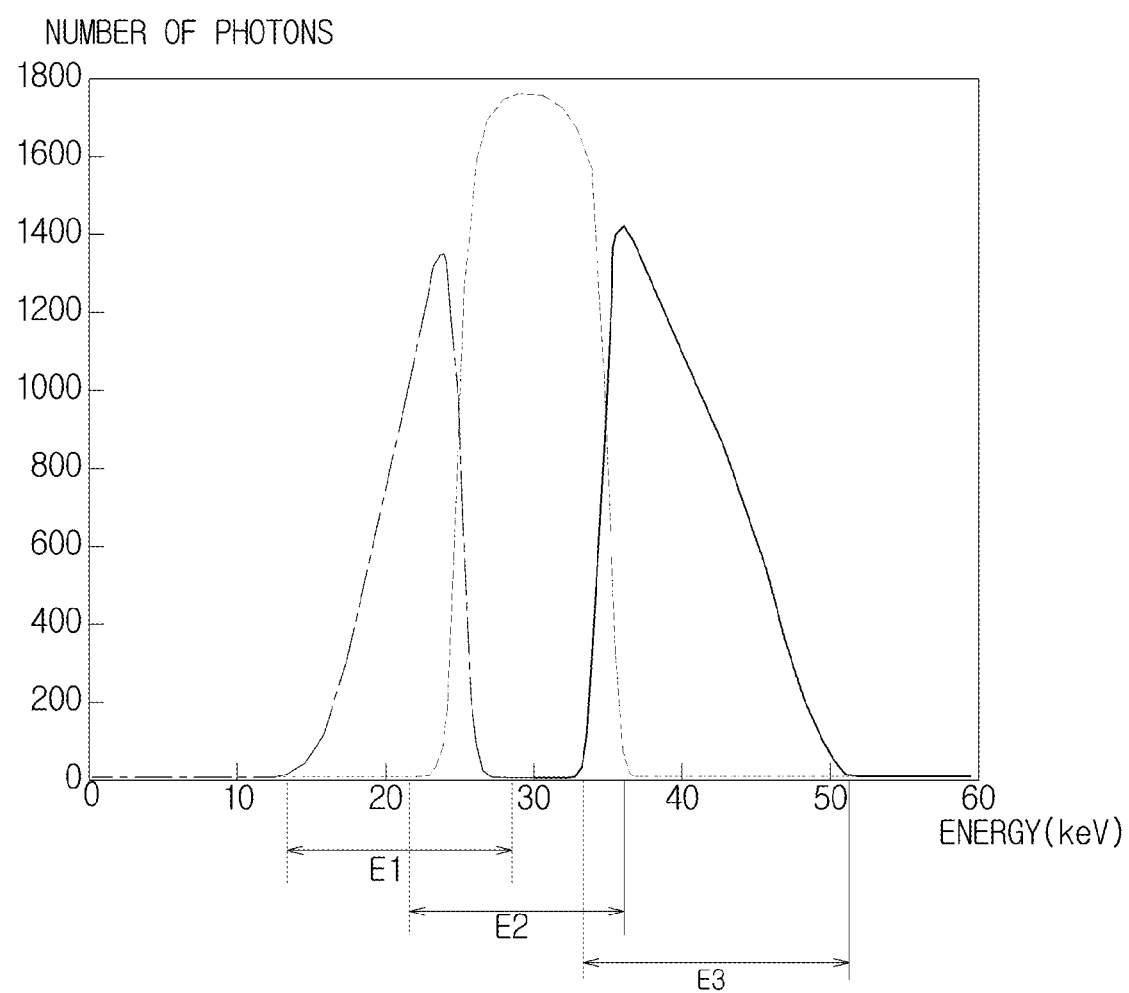
FIG. 4B is a graph showing an ideal spectrum for a case in which an X-ray detector of FIG. 4A divides X-rays according to energy bands, according to an exemplary embodiment.

FIG. 4A is a graph shows an energy spectrum of X-rays emitted by an X-ray generator, according to an exemplary embodiment. FIG. 4B graph shows an ideal spectrum for a case in which the X-ray detector divides X-rays of FIG. 4A according to energy bands, according to an exemplary embodiment.

For example, when the X-ray generator 110 generates X-rays at a tube voltage of 50 KVp and emits the X-rays after filtering a low energy band (i.e., about 0 to about 10 keV), the X-rays emitted from the X-ray generator 110 have an energy spectrum shown in FIG. 4A. An X-ray dose (number of photons) represented by the y axis of a graph D illustrated in FIG. 4A may be controlled by tube current and X-ray exposure time.

The X-ray imaging apparatus 100 may generate one image using all energy bands of X-rays having the spectrum shown in FIG. 4A. However, in order to increase a contrast between tissues, the X-rays having the spectrum shown in FIG. 4A may be divided according to a plurality of energy bands and X-ray images corresponding to the energy bands may be generated to acquire a multiple-energy X-ray image with a high contrast from the X-ray images.

For example, the X-ray detector 120 divides incident X-rays according to energy bands. In an exemplary embodiment, the X-ray detector 120 is implemented in a photon counting mode, and the X-ray detector 120 includes a plurality of comparators and a plurality of counters, corresponding to a plurality of energy bands, for one pixel region of the read-out circuit 122. A threshold voltage of each comparator is adjusted to a voltage corresponding to an energy band to be divided and each counter counts only photons having higher energy than energy corresponding to the threshold voltage, and thus, X-ray signals may be acquired on an energy band basis.

Alternatively, the X-ray generator 110 may emit X-rays of each energy band a plurality of times. However, according to an exemplary embodiment, since the X-ray detector 120 is implemented in a photon counting mode, the X-ray generator 110 emits X-rays having a plurality of different energy bands and the X-ray detector 120 divides detected X-rays according to energy bands. The X-ray data acquired by the X-ray detector 120 contains information regarding the number of photons per pixel for each energy band.

For example, when X-rays are divided to have three energy bands E1, E2, and E3, the X-ray spectrum shown in FIG. 4A is divided into three energy bands, as shown in FIG. 4B. Energy bands of X-rays emitted by the X-ray generator 110 may be determined based on the type or characteristics of the object. According to an exemplary embodiment, when the object is the breast, X-rays having an X-ray band of 10 to 50 keV may be emitted in order to use three energy bands E1, E2, and E3 shown in FIG. 4B.

However, an energy spectrum of actual detected X-rays may be distorted according to the response characteristics of the X-ray detector 120, unlike the ideal spectrums shown in FIGS. 4A and 4B.

In particular, when the X-ray detector 120 is implemented in a photon counting mode, a charge sharing or pile-up phenomenon may occur. The charge sharing or pile-up phenomenon may affect the response characteristics of the X-ray detector 120, thereby distorting X-ray data.

The charge sharing phenomenon refers to a phenomenon whereby electrons or holes generated from one photon having specific energy are detected from a plurality of pixel regions of the X-ray detector 120 such that one photon is recognized as a plurality of photons having lower energy than the specific energy.

The pile-up phenomenon refers to a phenomenon whereby a next photon is detected before acquisition of a signal regarding one photon is completed such that a signal regarding two photons is recognized as a signal regarding one photon.

Figure 5:
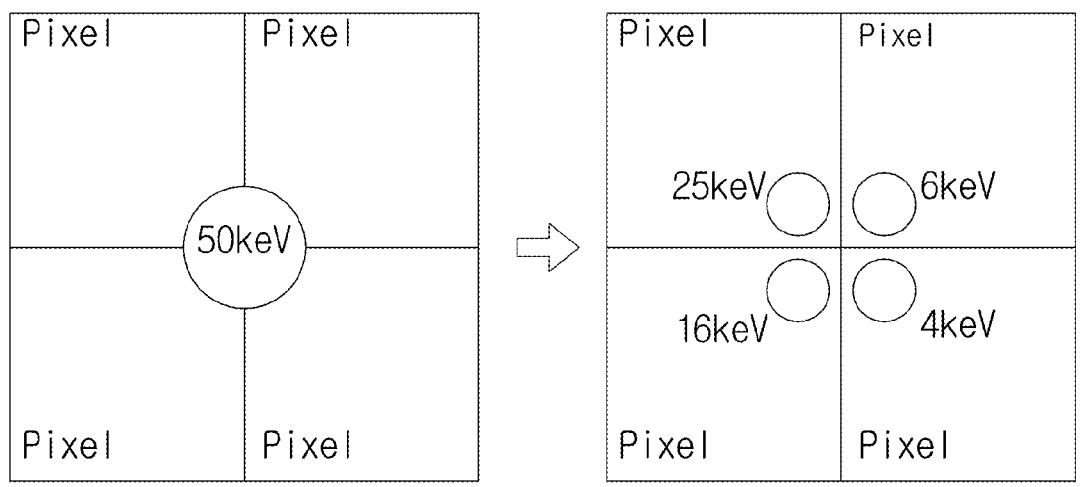
FIG. 5 is a schematic diagram showing a charge sharing phenomenon.

FIG. 5 is a schematic diagram showing a charge sharing phenomenon. Referring to FIG. 5, when a photon having energy of 50 keV is incident across four pixel regions of the X-ray detector 120, the X-ray detector 120 may recognize the one photon as four photons having lower energy than 50 keV. For example, the photon having energy of 50 keV may be recognized as four photons having energies of 25 keV, 6 keV, 16 keV, and 4 keV. In addition, a phenomenon whereby electric charges generated by one photon are separately incident upon a plurality of pixel regions regardless of an incident region of the photon is also regarded as the charge sharing phenomenon.

Figure 6A:
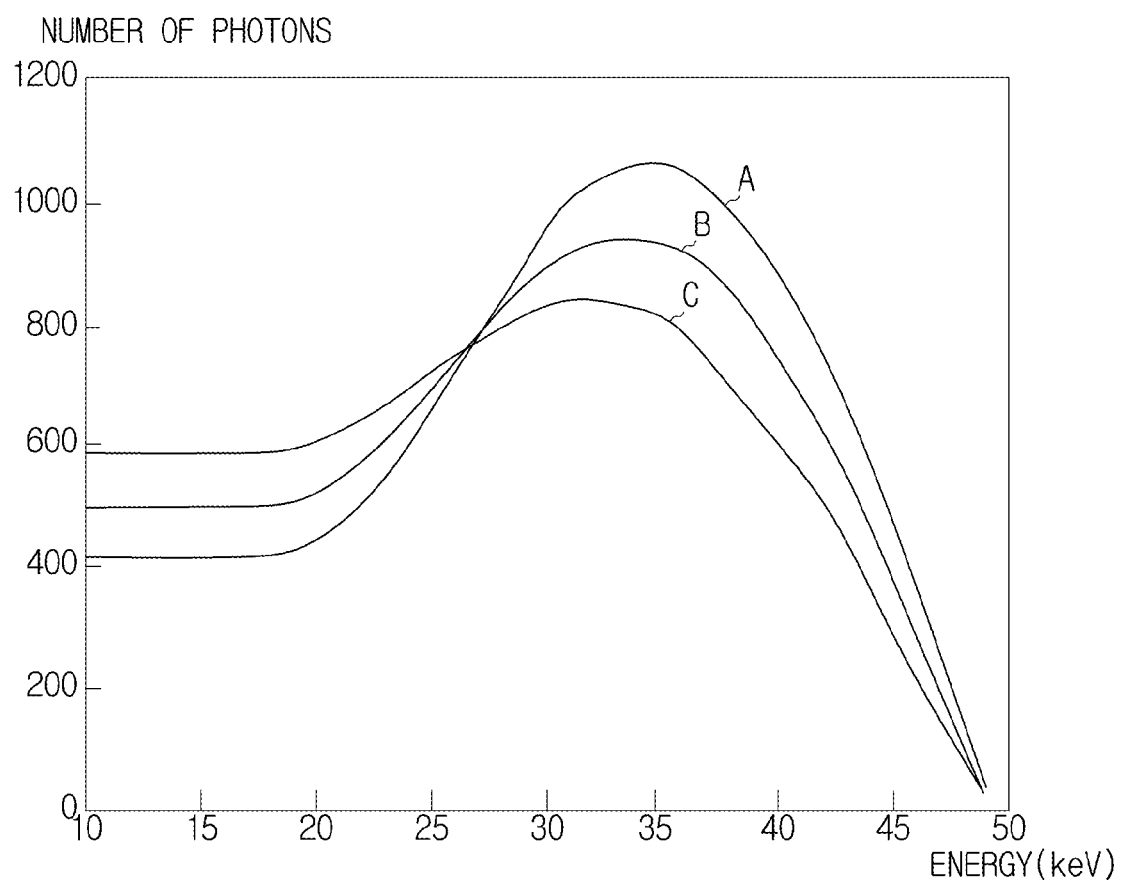
FIG. 6A is a graph showing a distorted spectrum with respect to energy bands of X-rays.
Figure 6B:
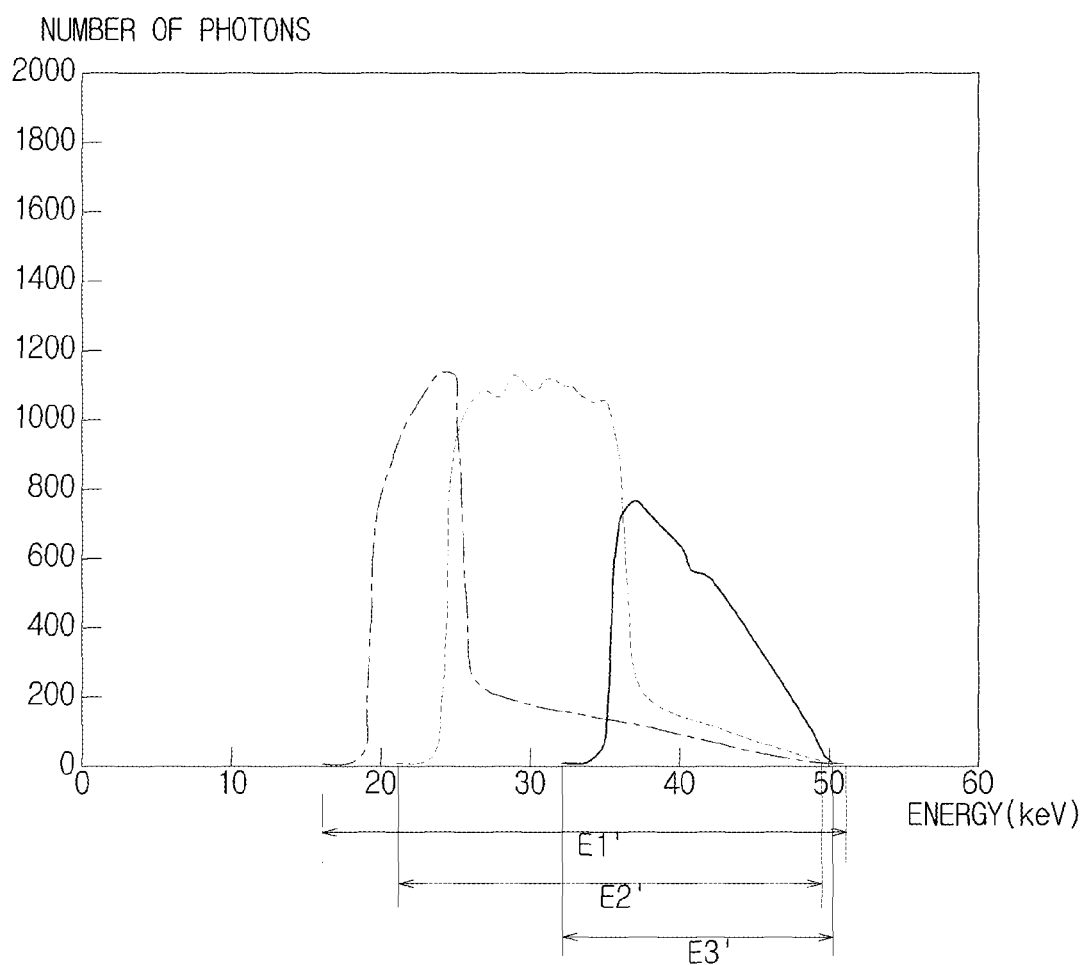
FIG. 6B is a graph showing a distorted spectrum obtained when X-rays are divided according to energy bands.

FIG. 6A is a graph showing a distorted spectrum with respect to energy bands of X-rays and FIG. 6B is a graph showing a distorted spectrum obtained when X-rays are divided according to energy bands. It is assumed that the distortion shown in FIGS. 6A and 6B is generated due to the charge sharing phenomenon.

When the charge sharing phenomenon occurs in the X-ray detector 120, a photon having higher energy is recognized as a plurality of photons having lower energy. Thus, the X-ray detector 120 detects the number of photons in a high energy region (about 30 to 40 keV) as less than in an actual spectrum and the number of photons in a low energy region (about 10 to 20 keV) as greater than in the actual spectrum, as shown in FIG. 6A. As seen from the graph of FIG. 6A, the distortion becomes worse toward a spectrum C from a spectrum A.

When X-rays detected by the X-ray detector 120 are divided according to a plurality of energy bands, distortion occurs due to influence of the charge sharing phenomenon, as shown in FIG. 6B. As described above, when the charge sharing phenomenon occurs, a photon having higher energy is perceived as a plurality of photons having lower energy, and thus, actual photons having higher energy are counted as photons having lower energy. Thus, in reality, some of the photons in an energy band E2 and some of photons in an energy band E3 may be counted as photons in an energy band E1. Thus, divided energy bands may be E1', E2', and E3' shown in FIG. 6B, thereby reducing X-ray energy separation characteristics.

According to an exemplary embodiment, the controller 130 of the X-ray imaging apparatus 100 may estimate the response characteristics of the X-ray detector 120 in advance and may inversely use the estimated response characteristics to correct the detected X-ray data, thereby correcting distortion in the X-ray data.

Hereinafter, a detailed structure and operation of the controller 130 will be described in detail.

Figure 7:
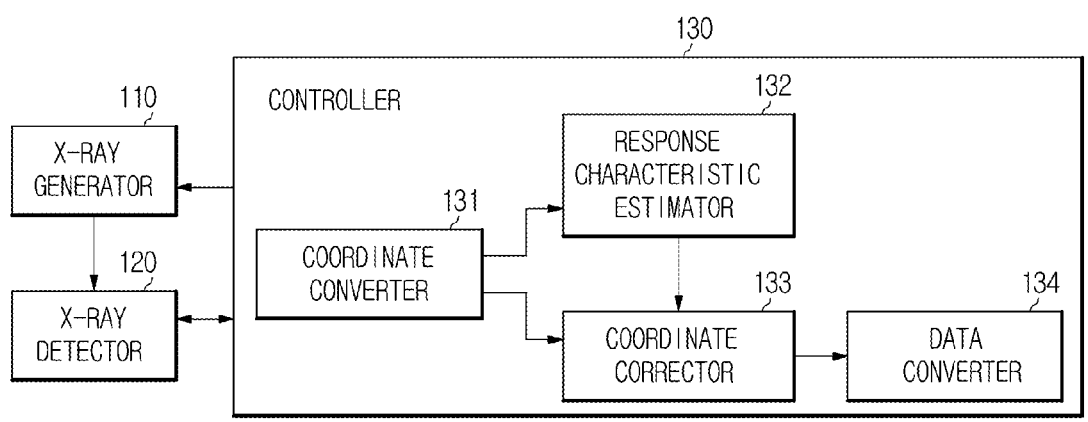
FIG. 7 is a control block diagram showing a controller of an X-ray imaging apparatus in detail according to an exemplary embodiment.

FIG. 7 is a control block diagram showing the controller 130 of an X-ray imaging apparatus in detail according to an exemplary embodiment.

Operations of the X-ray generator 110 and the X-ray detector 120 are described above with reference to FIG. 1, and thus, a detailed description thereof will be omitted.

Referring to FIG. 7, the controller 130 includes a coordinate converter 131 to convert X-ray data acquired by the X-ray detector 120 into coordinates, a response characteristic estimator 132 to estimate the response characteristic of the X-ray detector 120, a coordinate corrector 133 to correct the coordinates converted from the X-ray data using the estimated response characteristic, and a data converter 134 to convert the corrected coordinates into X-ray data.

The coordinate converter 131 converts the X-ray data acquired by the X-ray detector 120 into coordinates on a predetermined space. In an exemplary embodiment, for convenience of description, coordinates converted from X-ray data will be referred to as X-ray characteristic coordinates.

The predetermined space may be a space whereby the characteristics of X-ray data of each energy band are indicated. A coordinate conversion method may be based on a space conversion method of RGB data for a color image.

According to an exemplary embodiment, when the coordinate converter 131 uses a normalized coordinate system, coordinate conversion may be performed according to Expression 1 below.

$$d_1 = D_1/(D_1+D_2+D_3), d_2 = D_2/(D_1+D_2+D_3), d_3 = D_3/(D_1+D_2+D_3)$$ [Expression 1]

Here, $D_1$, $D_2$, $D_3$ are X-ray data corresponding to the number of photons per pixel for each energy band.

According to an exemplary embodiment, the X-ray imaging apparatus 100 may convert the X-ray data into X-ray characteristic coordinates via the coordinate converter 131 and may estimate the response characteristics of the X-ray detector 120 using the X-ray characteristic coordinates. When the X-ray data is corrected using the estimated response characteristics, the X-ray characteristic coordinates may be corrected instead of the X-ray data. When the X-ray data is converted into coordinates, if the response characteristics are estimated to correct data, data distortion may be corrected while minimizing reduction in X-ray image quality.

Figure 8A:
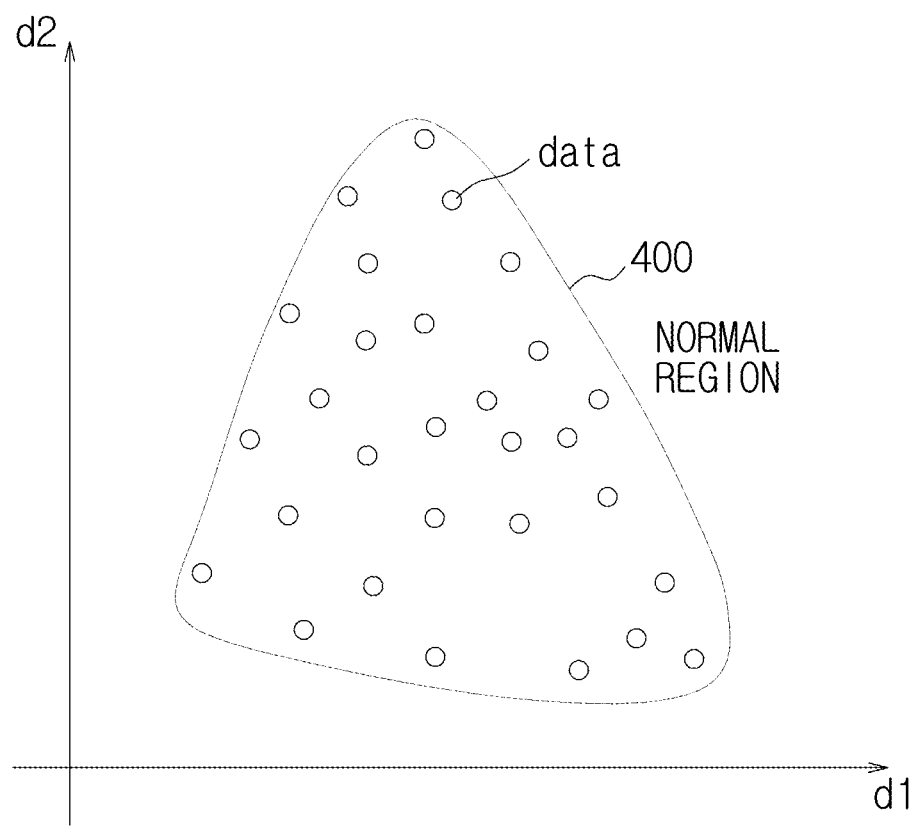
FIG. 8A shows a graph of X-ray data converted into coordinates when distortion does not occur.
Figure 8B:
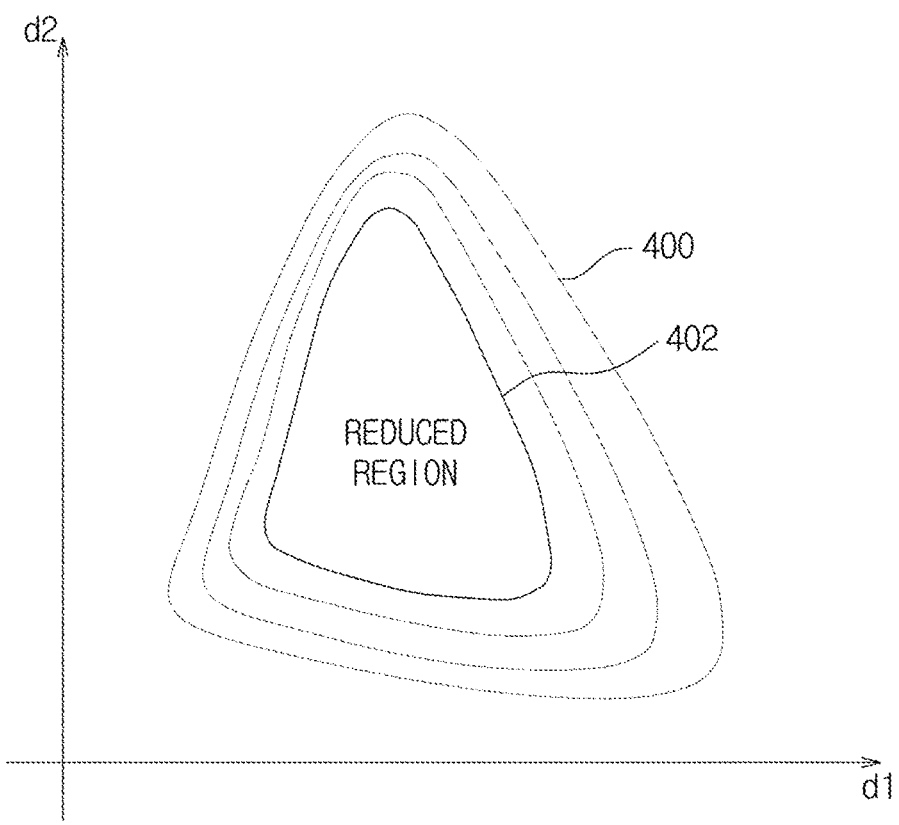
FIG. 8B shows a graph of X-ray data converted into coordinates when distortion occurs.

FIG. 8A shows a graph of X-ray data converted into coordinates when distortion does not occur and FIG. 8B shows a graph of X-ray data converted into coordinates when distortion occurs.

When the X-rays detected by the X-ray detector 120 are divided to have the energy bands E1, E2, and E3 and the distortion does not occur, as shown in FIG. 4B, the characteristics of X-ray data acquired by the X-ray detector 120 may be expressed in a region 400 of a predetermined space, as shown in FIG. 8A. The graph of FIG. 8A is illustrated according to a principle similar to an RGB color chart.

However, as shown in FIG. 6B, when overlap between energy bands occurs during division of X-rays, the X-ray data is distorted. A space 402 in which the characteristics of the X-ray data are expressed is reduced, as shown in FIG. 8B, from a space 400.

The response characteristic estimator 132 estimates the response characteristics of the X-ray detector 120 to estimate the distortion in advance. In detail, the response characteristic estimator 132 may acquire a plurality of measurement data and reference data regarding a phantom while varying a parameter (hereafter, a 'response characteristic parameter') which may influence the response characteristics of the X-ray detector 120 and may estimate a response characteristic function of the X-ray detector 120 using a relationship between the measurement data and the reference data.

The phantom is subjected to measurement, which is used for test of the performance of an X-ray imaging apparatus and maintenance of the X-ray imaging apparatus, and formed of various materials in various shapes. Thus, with regard to the X-ray imaging apparatus according to an exemplary embodiment, a type of the phantom is not particularly limited. The measurement data is acquired by detecting X-rays emitted by the X-ray detector 120 and having passed through the phantom and the reference data is acquired via simulation to which the same response characteristic parameter as in the acquisition of the measurement data is applied.

The response characteristic parameter may be a voltage of the X-ray detector 120, that is, a voltage applied between opposite ends of the detection device 121, a tube voltage of the X-ray generator 110, a spectrum length of X-rays emitted from the X-ray generator 110, or the like, but is not limited thereto. Thus, the response characteristic parameter may be any response characteristic parameter which influences the response characteristics of the X-ray detector 120.

For example, the voltage of the X-ray detector 120 may differ from $V_1$ to $V_n$ ($n \geq 2$, integer) to acquire the measurement data of the phantom and the simulation may be performed to acquire the reference data of the phantom at the voltage of the X-ray detector 120 from $V_1$ to $V_n$.

The response characteristic function of the X-ray detector 120 is estimated using the relationship between the measurement data and the reference data.

The reference data and the measurement data for a plurality of different tube voltage sets, a plurality of different X-ray spectrum sets, or the like may be acquired to estimate the response characteristic function of the X-ray detector 120.

Alternatively, a plurality of response characteristic parameters may be set as one set, and the reference data and the measurement data for a plurality of sets while varying at least one of the response characteristic parameters.

The response characteristic estimation by using a phantom may be performed once before the X-ray imaging apparatus 100 begins to be used, may be periodically performed, or may be performed whenever the X-ray imaging apparatus 100 is used. In an exemplary embodiment, a number and times of the response characteristic estimation performed by the response characteristic estimator 132 is not particularly limited.

The coordinate corrector 133 corrects X-ray data for the object using the estimated response characteristics. The coordinate corrector 133 may correct X-ray data that is converted into X-ray characteristic coordinates by the coordinate converter 131. That is, when X-rays having passed through the object are detected by the X-ray detector 120, are converted into X-ray data indicating the number of photons for each energy band, and are transmitted to the controller 130, the coordinate converter 131 of the controller 130 converts the X-ray data into coordinates on a predetermined space, that is, X-ray characteristic coordinates. The coordinate corrector 133 may correct the X-ray characteristic coordinates.

The coordinate corrector 133 inversely uses the response characteristic function estimated by the response characteristic estimator 132 to correct the X-ray data. FIG. 9 is a schematic diagram showing a relationship between a function estimated by the response characteristic estimator 132 and a function used by the coordinate corrector 133.

Referring to FIG. 9, when X-ray data divided to have energy bands E1, E2, and E3 is converted into coordinates on a predetermined space, the characteristics of the X-ray data may be expressed in a region 404. When overlap between energy bands occurs due to the response characteristics of the X-ray detector 120, a space in which the characteristics of the X-ray data are expressed is reduced to a region 406. The response characteristic function estimated by the response characteristic estimator 132 corresponds to a function which converts the region 404 into the region 406', and thus, an inverse of the response characteristic function is used in order to convert the region 406 into the region 404.

Thus, the coordinate corrector 133 calculates an inverse (hereinafter, referred to as a 'response characteristic inverse function') of a function estimated by the response characteristic estimator 132 and corrects the X-ray data by applying the response characteristic inverse function to the X-ray characteristic coordinates.

Alternatively, the response characteristic estimator 132 may calculate the response characteristic inverse function and transmit the response characteristic inverse function to the coordinate corrector 133. Then, the coordinate corrector 133 may apply the response characteristic inverse function directly to the X-ray characteristic coordinates.

The data converter 134 converts the X-ray characteristic coordinates corrected by the coordinate corrector 133 into the X-ray data which are transmitted to an image processor to perform an image process for generation of an X-ray image.

Correction of X-ray data via the coordinate converter 131, the response characteristic estimator 132, and the coordinate corrector 133 may be represented by, for example, Expression 2 below.

$$D_{corrected} = P^{-1} \cdot F^{-1} \cdot P \cdot D_{measured} \quad \text{[Expression 2]}$$

$D_{measured}$ is X-ray data for an object, acquired by the X-ray detector 120, P is a function for conversion of the X-ray data into X-ray characteristic coordinates, F is a response characteristic function, and $D_{corrected}$ is final corrected X-ray data.

Thus, the X-ray imaging apparatus 100 according to an exemplary embodiment may convert the X-ray data $D_{measured}$ of the object into X-ray characteristic coordinates using function P, correct the converted X-ray characteristic coordinates using the response characteristic inverse function $F^{-1}$, and convert the corrected X-ray characteristic coordinates into X-ray data using an inverse of a function P, to acquire the X-ray data $D_{corrected}$, distortion of which is corrected.

Figure 10:
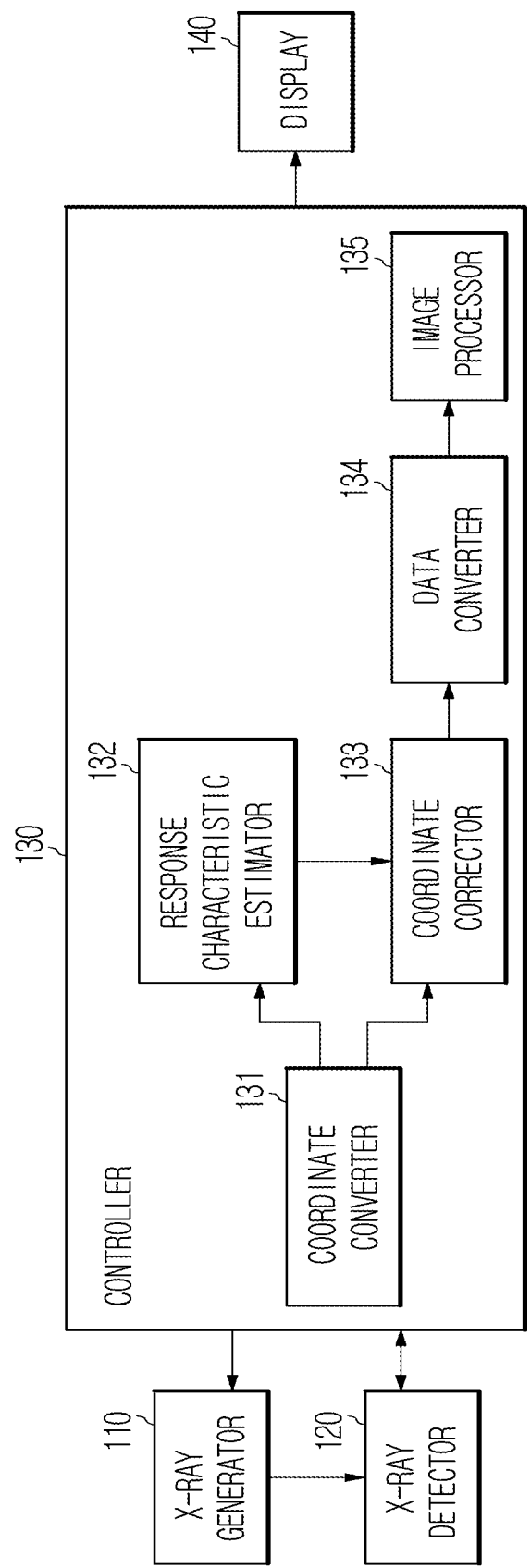
FIG. 10 is a control block diagram showing an X-ray imaging apparatus in more detail.

FIG. 10 is a control block diagram showing the X-ray imaging apparatus 100 in more detail.

Referring to FIG. 10, the X-ray imaging apparatus 100 according to an exemplary embodiment may further include an image processor 135 to generate a multiple-energy X-ray image, which is included in the controller 130, and may further include a display 140 to display the X-ray image generated by the image processor 135. The other elements have been described already, and thus, a detailed description thereof will be omitted.

The image processor 135 may receive corrected X-ray data from the data converter 134 to generate the multiple-energy X-ray image. The transmitted X-ray data includes X-ray signals for each energy band. For example, when X-rays detected by the X-ray detector 120 are divided to have energy bands E1, E2, and E3, the X-ray data transmitted to the image processor 135 contains information regarding the number of photons belonging to the energy band E1, the number of photons belonging to the energy band E2, and the number of photons belonging to the energy band E3. The number of photons is counted on a pixel basis.

Hereinafter, a method of generating the multiple-energy X-ray image by the image processor 135 will be described with regard to an exemplary embodiment.

Figure 11:
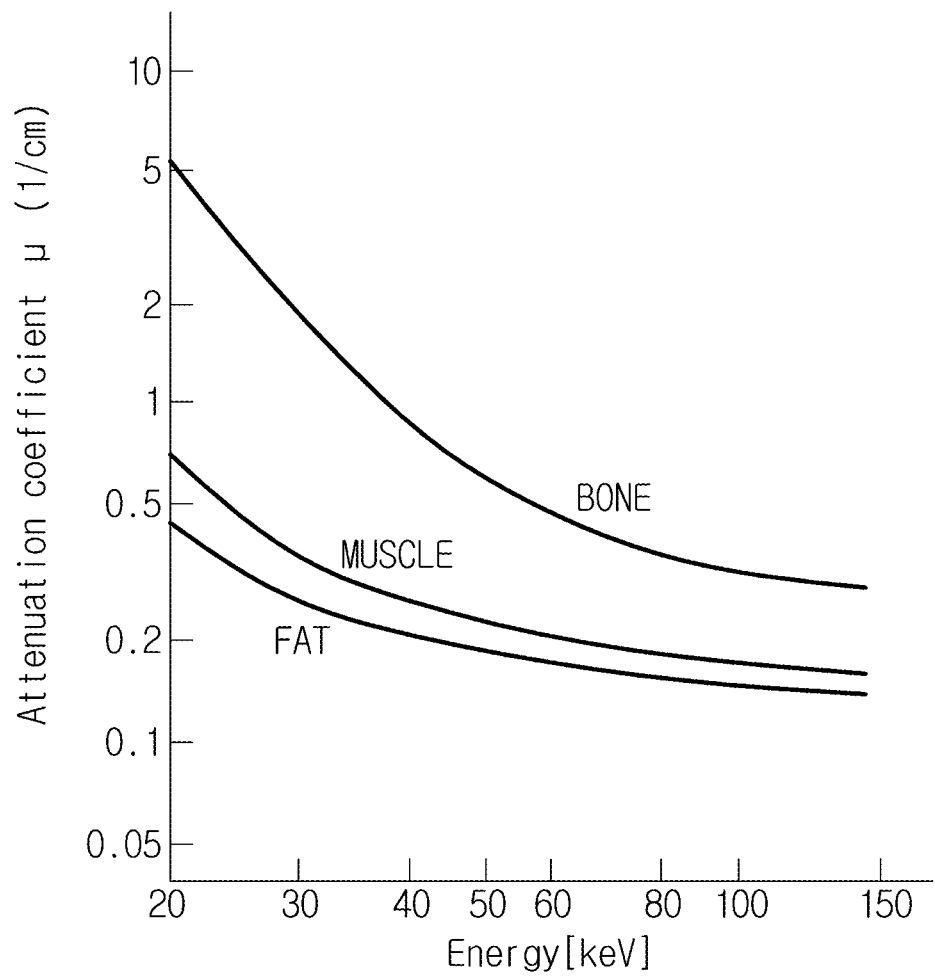
FIG. 11 is a schematic graph showing variation in an X-ray attenuation coefficient according to materials constituting the human body.

FIG. 11 is a schematic graph showing variation in an X-ray attenuation coefficient according to materials constituting the human body.

As described above, X-ray permeability may differ according to the characteristics of materials through which X-rays pass, which is numerically represented as an attenuation coefficient.

FIG. 11 shows curves indicating variation in an X-ray attenuation coefficient according to X-ray energy with respect to bone, muscle, and fat. As shown in FIG. 11, the variation in an X-ray attenuation coefficient differs with respect to bone, muscle, and fat, and a difference in X-ray attenuation coefficients for the respective materials differs according to X-ray energy.

FIG. 11 shows variation in an X-ray attenuation coefficient according to X-ray energy with respect to bone, muscle, and fat only. However, variation in an X-ray attenuation coefficient differs between various soft tissues including fat. Thus, materials having different attenuation characteristics may be extracted from one image using a plurality of image signals of different energy bands.

When an attenuation coefficient of X-rays including $N_0$ photons having energy E is $\mu(E)$, the number N of photons after the X-rays pass through an object having a thickness T may be given according to Expression 3 below.

$$N = N_0 * e^{-\mu(E)T} \quad \text{[Expression 3]}$$

When the number of types of materials through which X-rays pass is M, if a thickness of $m_{th}$ material is $T_m$, Expression 3 may be rewritten as Expression 4 below.

$$N = N_0 * e^{-\{\mu_1(E)T_1 + \mu_2(E)T_2 + \ldots + \mu_M(E)TM\}} \quad \text{[Expression 4]}$$

Based on Expression 4, pixel values of an image are determined by dividing opposite sides by a measurable value $N_0$ and applying antilogarithm (−log). Likewise, when a number L of X-ray images are acquired with respect a number L of different energies $E_1, E_2, \ldots,$ and $E_L$, a pixel value $I(E_1)$ may be given according to Expression 5 below.

$$I(E_1) = -\log(N(E_1)/N_0) \quad \text{[Expression 5]}$$
$$= \mu_1(E_1)T_1 + \mu_2(E_2)T_2 + \ldots + \mu_M(E_1)T_M$$

Thus, L equations such as Expression 5 above may be obtained for the number L of X-ray images with respect to each pixel, which may be given according to a determinant, for example, Expression 6 below.

$$I = \mu \cdot T \quad \text{[Expression 6]}$$

Thus, when L=M, an image separated per material may be obtained by calculating a determinant $T = \mu^{-1} \cdot I$. Expression 6 is derived when it is assumed that an ideal monochromatic X-ray image is used. However, when an X-ray image having a specific energy band is used, Expression 6 may be modified and used appropriately for the case.

The multiple-energy X-ray image generated by the image processor 135 may be at least one image separated per material or may be a characteristic image indicating the image separated per material as one image. The characteristic image may be used to distinguish a plurality of materials in one image via color mapping, brightness adjustment, or the like.

The multiple-energy X-ray image generated by the image processor 135 may be displayed through the display 140.

Hereinafter, a method of controlling an X-ray imaging apparatus will be described with regard to an exemplary embodiment.

Figure 12:
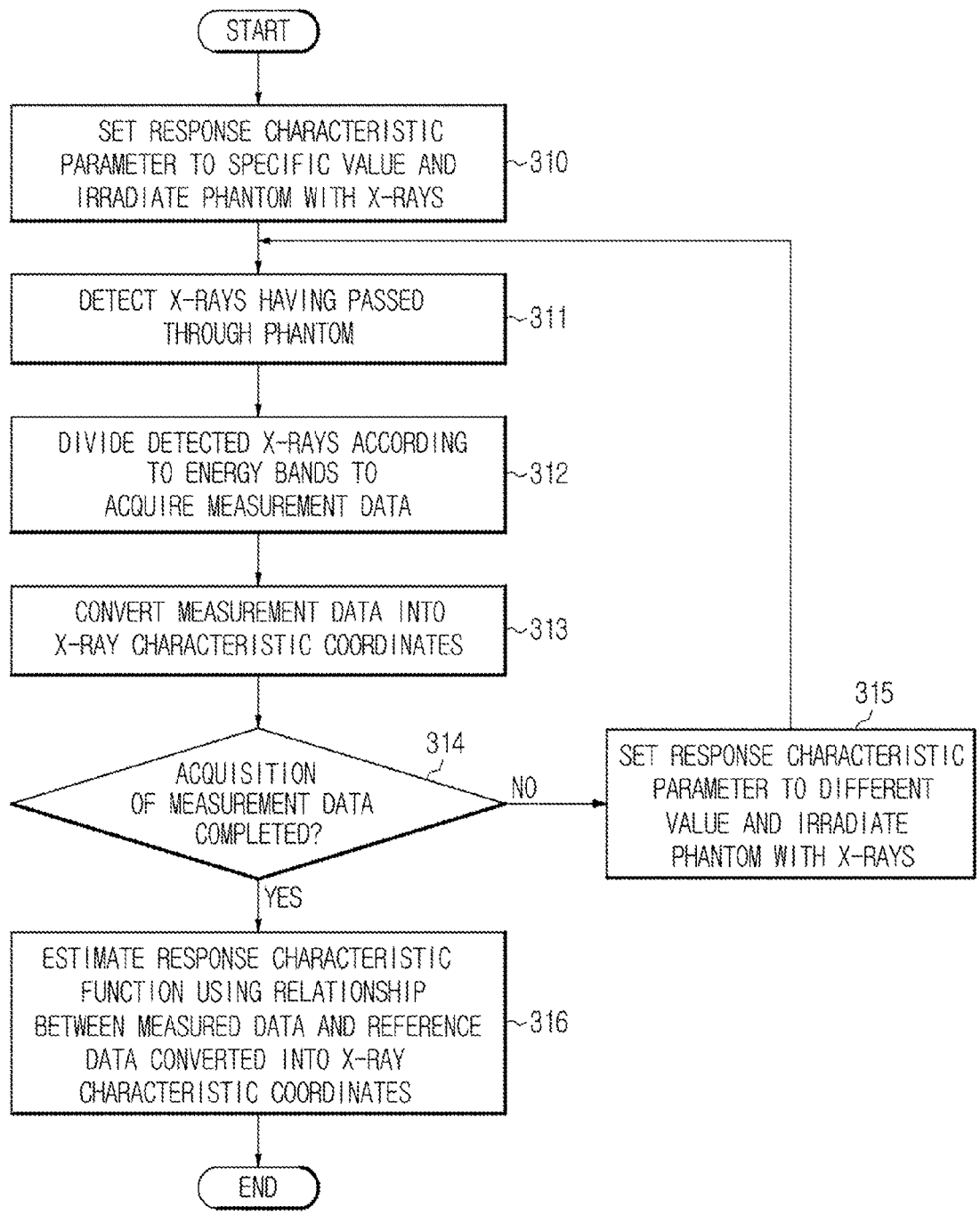
FIG. 12 is a flowchart of a method of estimating response characteristics of an X-ray detector in a method of controlling an X-ray imaging apparatus according to an exemplary embodiment.

FIG. 12 is a flowchart of a method of estimating response characteristics of the X-ray detector 120 in a method of controlling an X-ray imaging apparatus according to an exemplary embodiment.

Referring to FIG. 12, a response characteristic parameter is set to a specific value and a phantom is irradiated with X-rays in operation 310. The response characteristic parameter is a parameter that influences the response characteristics of the X-ray detector 120, and is a voltage of the X-ray detector 120, that is, a voltage applied between opposite ends of the detection device 121, a tube voltage of the X-ray generator 110, a spectrum length of X-rays emitted from the X-ray generator 110, or the like. A parameter may be predefined or may be arbitrarily set. A shape or material of the phantom is not particularly limited. The X-rays emitted to the phantom are broadband X-rays having a plurality of energy bands.

In operation 311, X-rays having passed through the phantom are detected and divided according to a plurality of energy bands to acquire measurement data, in operation 312. The divided energy band may be set in advance. The measurement data contains the number of photons per energy band, and the number of photons is measured for each pixel.

The measurement data is converted into coordinates in a predefined space, that is, X-ray characteristic coordinates, in operation 313. The predefined space may be a space by the characteristics of X-ray data of each energy band are indicated.

Whether acquisition of the measurement data is completed is determined in operation 314. According to an exemplary embodiment, when X-rays are emitted and detected with respect to all predefined response characteristic parameter sets to acquire the measurement data, it may be determined that the acquisition of the measurement data is completed.

When the acquisition of the measurement data is not completed (No), the response characteristic parameter is set to a different value, and the phantom is irradiated with X-rays, in operation 315. Operations 311 through 314 are repeatedly performed.

When the acquisition of the measurement data is completed (YES), a response characteristic function of the X-ray detector 120 is estimated using a relationship between the measurement data and the reference data which are converted into X-ray characteristic coordinates in operation 316. The reference data is X-ray data acquired via simulation using the same response characteristic parameter as a parameter that is set during acquisition of the measurement data.

Figure 13:
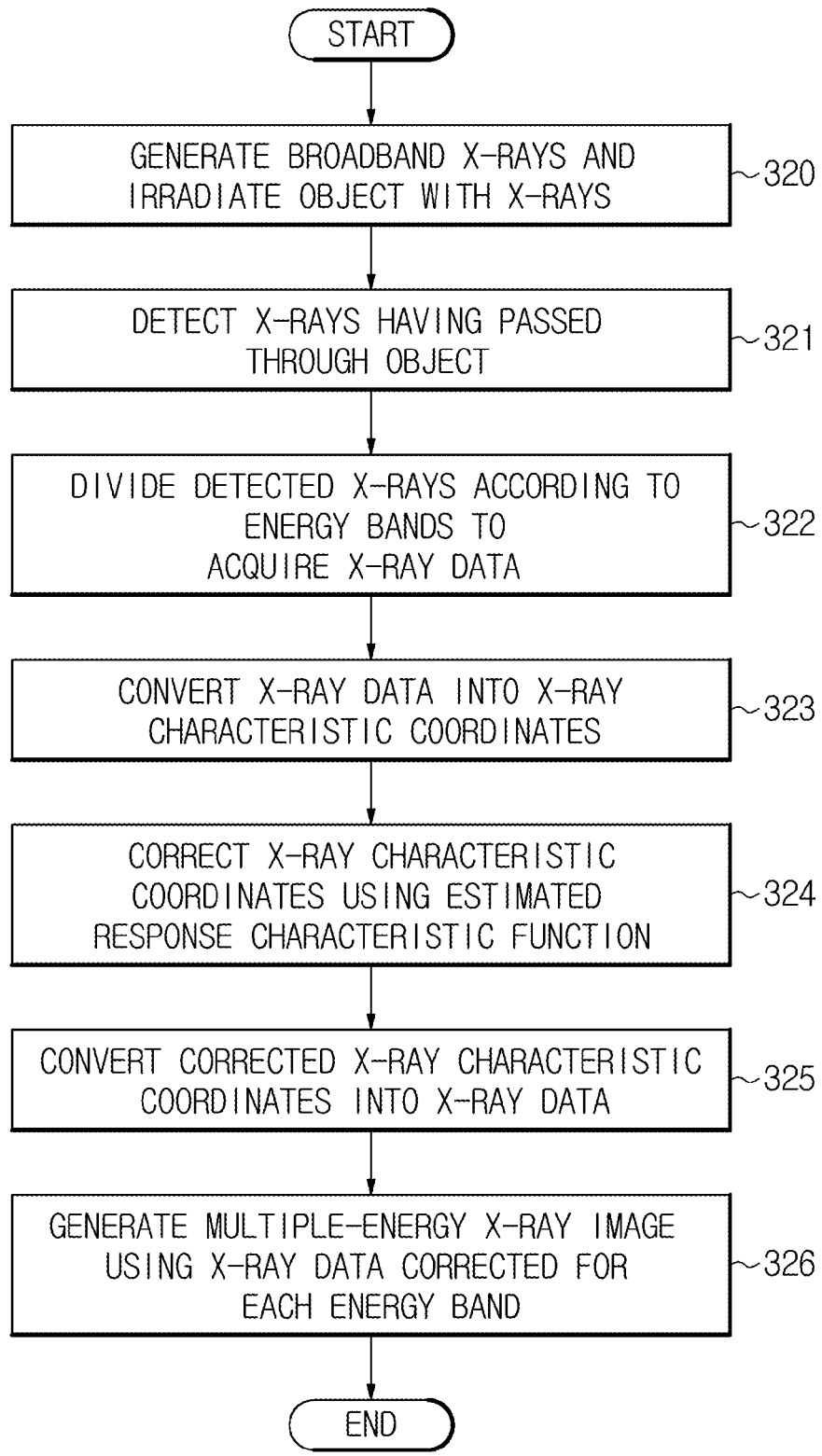
FIG. 13 is a flowchart of a method of correcting X-ray data using an estimated response characteristic function in a method of controlling an X-ray imaging apparatus according to an exemplary embodiment.

FIG. 13 is a flowchart of a method of correcting X-ray data using an estimated response characteristic function in a method of controlling an X-ray imaging apparatus according to an exemplary embodiment.

Referring to FIG. 13, broadband X-rays having a plurality of energy bands are generated and emitted to an object in operation 320. Energy bands of the broadband X-rays may be set in different ways according to characteristics of the object.

X-rays having passed through the object are detected in operation 321. The detected X-rays are divided according to a plurality of energy bands to acquire X-ray data in operation 322. The energy bands may be set according to the type of object in advance or may be set via auto exposure control (AEC) based on the thickness, intensity, or the like of the object. The X-ray data may indicate the number of photons for each energy band and may be acquired per pixel.

The acquired X-ray data is converted into X-ray characteristics coordinates in operation 323. In operation 324, the X-ray characteristic coordinates are corrected using the response characteristic function estimated in the process shown in FIG. 11. In detail, as described with reference to FIG. 9, the estimated response characteristic function shows a relationship between normal X-ray characteristic coordinates and distorted X-ray characteristic coordinates. In order to correct the distorted X-ray characteristic coordinates to the normal X-ray characteristic coordinates, the estimated response characteristic function needs to be inversely used. That is, an inverse of the estimated response characteristic function may be calculated and a response characteristic inverse function may be applied to the X-ray characteristic coordinates to acquire X-ray characteristic coordinates.

The corrected X-ray characteristic coordinates are converted into X-ray data in operation 325. A multiple-energy X-ray image is generated using X-ray data corrected for each energy band, in operation 326. The multiple-energy X-ray image may be at least one image of the object, separated per material or may be an image indicating the image separated per material as one image.

In the above-described exemplary embodiments, an X-ray detector uses a direct conversion type, a hybrid device, and a photon counting mode, which is merely an X-ray imaging apparatus according to an exemplary embodiment. The type of distortion to be corrected by the X-ray imaging apparatus is not limited. Thus, an X-ray detector using methods, other than described above, may also be used to correct data distortion according to response characteristics.

In the above-described exemplary embodiments, a case in which detected X-rays are divided according to a plurality of energy bands has been described. However, exemplary embodiments are not limited thereto, and may be used when a single energy band is used.

As described above, an X-ray imaging apparatus and a method of controlling the same according to exemplary embodiments may estimate the energy response characteristics of an X-ray detector and may correct data distortion based on the estimated response characteristics to effectively correct and/or compensate for distortion of an X-ray image.

Although a few exemplary embodiments have been shown and described, exemplary embodiments are not limited thereto. It would be appreciated by those skilled in the art that changes may be made in these exemplary embodiments without departing from the principles and spirit of the disclosure, the scope of which is defined in the claims and their equivalents.

What is claimed is:

1. An X-ray imaging apparatus comprising:
   an X-ray generator configured to generate and emit X-rays;
   an X-ray detector configured to detect the emitted X-rays and acquire X-ray data; and
   a controller configured to convert measurement data acquired by detecting X-rays by the X-ray detector and reference data acquired via simulation into X-ray characteristic coordinates as coordinates on a predefined space and to estimate a response characteristic function of the X-ray detector from a relationship between the converted reference data and the converted measurement data.

2. The X-ray imaging apparatus according to claim 1, wherein the measurement data comprises the X-ray data acquired by setting a response characteristic parameter influencing response characteristics of the X-ray detector to a predefined value, irradiating a phantom with the X-rays by the X-ray generator, and detecting the X-rays having passed through the phantom by the X-ray detector.

3. The X-ray imaging apparatus according to claim 2, wherein the reference data comprises the X-ray data acquired via the simulation using the same response characteristic parameter as the response characteristic parameter set during acquisition of the measurement data.

4. The X-ray imaging apparatus according to claim 3, wherein the response characteristic parameter is set to different values, and the measurement data and the reference data are acquired a plurality of times.

5. The X-ray imaging apparatus according to claim 3, wherein the response characteristic parameter comprises at least one of a tube voltage of the X-ray generator, a voltage applied between opposite ends of a detection device of the X-ray detector, and a spectrum of the X-rays emitted by the X-ray generator.

6. The X-ray imaging apparatus according to claim 1, wherein the controller corrects X-ray data of an object using the estimated response characteristic function.

7. The X-ray imaging apparatus according to claim 6, wherein the controller converts the X-ray data of the object into the X-ray characteristic coordinates and corrects the converted X-ray characteristic coordinates based on the estimated response characteristic function.

8. The X-ray imaging apparatus according to claim 7, wherein the controller calculates a response characteristic inverse function as an inverse of the estimated response characteristic function and applies the response characteristic inverse function to the converted X-ray characteristic coordinates.

9. The X-ray imaging apparatus according to claim 8, wherein the controller converts the corrected X-ray characteristic coordinates into a converted X-ray data and generates an X-ray image using the converted X-ray data.

10. A method of controlling an X-ray imaging apparatus, the method comprising:
    acquiring measurement data by detecting X-rays by an X-ray detector;
    acquiring reference data via simulation using the same value of a response characteristic parameter as a specific value of a response characteristic parameter set during acquisition of the measurement data;
    converting each of the measurement data and the reference data into X-ray characteristic coordinates as coordinates on a predefined space; and
    estimating a response characteristic function of the X-ray detector from a relationship between the converted measurement data and the converted reference data.

11. The method according to claim 10, wherein the acquiring the measurement data comprises:
    setting the response characteristic parameter to the specific value and irradiating a phantom with X-rays; and
    detecting the X-rays having passed through the phantom to acquire X-ray data.

12. The method according to claim 11, wherein the acquiring the measurement data comprises:
    setting the response characteristic parameter to different values; and
    acquiring the measurement data a plurality of times.

13. The method according to claim 11, wherein the response characteristic parameter comprises at least one of a tube voltage of an X-ray generator, a voltage applied between opposite ends of a detection device of the X-ray detector, and a spectrum of the X-rays emitted by the X-ray generator.

14. The method according to claim 10, further comprising correcting X-ray data of an object based on the estimated response characteristic function.

15. The method according to claim 14, wherein the correcting the X-ray data comprises acquiring the X-ray data of the object and converting the X-ray data into the X-ray characteristic coordinates.

16. The method according to claim 15, wherein the correcting the X-ray data further comprises calculating a response characteristic inverse function as an inverse of the estimated response characteristic function.

17. The method according to claim 16, wherein the correcting the X-ray data further comprises applying the response characteristic inverse function to the X-ray characteristic coordinates converted from the X-ray data.

18. An X-ray imaging apparatus comprising:
    an X-ray generator configured to irradiate X-rays;
    an X-ray detector configured to detect the X-rays; and
    a controller which is configured to perform operations of:
    setting an imaging condition by selecting a response characteristic parameter of at least one of the X-ray generator and the X-ray detector;
    acquiring measurement data by an X-ray imaging a phantom based on the response characteristic parameter;
    acquiring reference data by performing a simulation of X-ray acquisition based on the response characteristic parameter;
    estimating a response characteristic function of the X-ray detector by comparing the measurement data and the reference data;

determining an inverse of the response characteristic function; and compensating X-ray data of an object being X-ray imaged by applying the inverse of the response characteristic function to the X-ray data of the object.

19. The X-ray imaging apparatus of claim 18, wherein the processor is further configured to perform operations of:

converting the measurement data into a first set of X-ray characteristic coordinates;

converting the reference data into a second set of X-ray characteristic coordinates;

determining the response characteristic function by comparing the first set with the second set;

converting the X-ray data of the object into a third set of X-ray characteristic coordinates;

correcting the third set of X-ray characteristic coordinates by using the determined response characteristic function;

applying the inverse of the determined response characteristic function to a corrected third set of X-ray characteristic coordinates of the object;

obtaining a compensated X-ray data of the object; and generating an X-ray image of the object from the compensated X-ray data.

* * * * *